US007678789B2

(12) United States Patent
Feenstra et al.

(10) Patent No.: US 7,678,789 B2
(45) Date of Patent: Mar. 16, 2010

(54) [1,2,4]-DITHIAZOLI(DI)NE DERIVATIVES, INDUCERS OF GLUTHATHIONE-S-TRANSFERASE AND NADPH QUINONE OXIDO-REDUCTASE, FOR PROPHYLAXIS AND TREATMENT OF ADVERSE CONDITIONS ASSOCIATED WITH CYTOTOXICITY IN GENERAL AND APOPTOSIS IN PARTICULAR

(75) Inventors: Roelof W. Feenstra, Weesp (NL); Hiskias G. Keizer, Weesp (NL); Maria L. Pras-Raves, Weesp (NL); Bernard J Van Vliet, Weesp (NL); Gustaaf J. M. Van Scharrenburg, Weep (NL)

(73) Assignee: Solvay Pharmaceuticals B.V., Weesp (NL)

( * ) Notice: Subject to any disclaimer, the term of this patent is extended or adjusted under 35 U.S.C. 154(b) by 523 days.

(21) Appl. No.: 11/349,910

(22) Filed: Feb. 9, 2006

(65) Prior Publication Data

US 2006/0194846 A1 Aug. 31, 2006

Related U.S. Application Data

(60) Provisional application No. 60/651,661, filed on Feb. 11, 2005.

(51) Int. Cl.
*A61K 31/541* (2006.01)
*A61K 31/5377* (2006.01)
*A61K 31/496* (2006.01)
*A61K 31/4535* (2006.01)
*A61K 31/4436* (2006.01)
*A61K 31/41* (2006.01)
*C07D 417/04* (2006.01)
*C07D 413/04* (2006.01)
*C07D 285/01* (2006.01)

(52) U.S. Cl. ............ 514/222.2; 514/236.8; 514/254.02; 514/326; 514/342; 514/360; 544/60; 544/134; 544/367; 546/209; 546/268.4; 548/123

(58) Field of Classification Search ................ 548/523, 548/123, 126; 546/268.4; 514/341, 362
See application file for complete search history.

(56) References Cited

FOREIGN PATENT DOCUMENTS

| GB | 1351412 | 5/1974 |
|----|---------|--------|
| JP | 48028470 | 4/1973 |
| JP | 55081804 | 6/1980 |
| JP | 57183770 A * | 11/1982 |
| JP | 08027148 | 1/1996 |

OTHER PUBLICATIONS

Remington et al., The Science and Practice of Pharmacy, 2000, Lippincott Williams and Wilkins, 20th, 218-220.*

Vippagunta, et al., Crystalline solids, 2001, Advanced Drug Delivery Reviews, 48, 1 and 18.*
Haynes et al., New Chemosterilants for Boll Weevils, U.S. Agricultural Research Service, South Reg. [Rep], 1976, vol. 30, p. 6.*
Patani et al., Bioisosterism: A Rational Approach in Drug Design, 1996, Chem. Rev., 96, pp. 3147-3176.*
Frank D. King, Medicinal Chemistry: Principles and Practice, *The Royal Society of Chemistry*, ISBN 0-85186-494-5, pp. 214-217 (1994).
Valentino J. Stella, Prodrugs as therapeutics, *Expert Opin. Ther. Patents*, 14(3), pp. 277-280 (2004).
Peter Ettmayer, et al., Lessons Learned From Marketed and Investigational Prodrugs, *Journal of Medicinal Chemistry*, vol. 47, No. 10, pp. 2393-2404 (2004).
M. H. Bickel, The Pharmacology and Biochemistry of N-Oxides, *Pharmacological Reviews*, vol. 21, No. 4, pp. 325-355 (1969).
Benjamin Drukarch, et al., Anethole dithiolethione prevents oxidative damage in gluthathione-depleted astrocytes, *European Journal of Pharmacology*, pp. 259-262 (1997).
Steven Duffy, et al., Activation of Endogenous Antioxidant Defenses in Neuronal Cells Prevents Free Radical-Medicated Damage, *Journal of Neurochemistry*, vol. 71, No. 1, pp. 69-77 (1998).
Hans J. Prochaska, et al., Direct Measurement of NAD(P)H: Quinone Reductase from Cells Cultured in Microtiter Wells: A Screening Assay for Anticarcinogenic Enzyme Inducers, *Analytical Biochemistry*, vol. 169, pp. 328-336 (1988).
Joachim Goerdeler, et al., Uber Thiocarbamoyl-isothiocyanate, II², *Chemische Berichte*, vol. 103, pp. 3392-3407 (1970).
J. von Braun, et al., *Berichte Der Deutsche Chemischen Gesellschaft*, vol. 36, pp. 2258-2274 (1903).
Argyropoulos, N. G.: "Product Class 2: 1,2,4-Dioxazoles, 1,2,4-Oxathiazoles and 1,2,4-Dithiazoles," *Science of Synthesis*, vol. 13-2, 2004, pp. 29-71, XP-009067608.

(Continued)

*Primary Examiner*—Kamal A Saeed
*Assistant Examiner*—Kristin Bianchi
(74) *Attorney, Agent, or Firm*—Finnegan, Henderson, Farabow, Garrett & Dunner, L.L.P.

(57) ABSTRACT

The present invention relates to 5-imino-5H-[1,2,4]-dithiazol-3-yl-amine and [1,2,4]-dithiazolidine-3,5-diylidene-diamine derivatives as inducers of gluthathione-S-transferase (GST) and NADPH quinone oxidoreductase (NQO), to methods for the preparation of these compounds and to novel intermediates useful for the synthesis of said [1,2,4]-dithiazoli(di)ne derivatives. The invention also relates to the use of a compound disclosed herein for the treatment of adverse conditions associated with cytotoxicity in general and apoptosis in particular. The invention relates to compounds of the general formula (I):

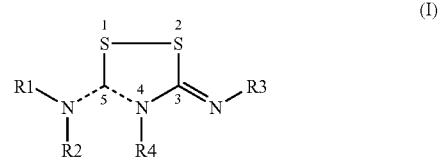

wherein
wherein the symbols have the meanings given in the specification.

6 Claims, No Drawings

OTHER PUBLICATIONS

Goerdeler, J., et al.: "3.5-Bis-thiocarbamoylimino-1.2.4-dithiazolidine: Verbindungen vom 'no-bond resonance'-Typ?," *Chem. Ber.*, vol. 105, 1972, pp. 1568-1577, XP-009067623.

Goerdeler, J., et al.: "Cycloadducts from 3-Imino-3H-1,2,4-dithiazoles and Nitriles: Conditions of Preparation and Structure," *Chem. Ber.* vol. 118, 1985, pp. 3241-3247, XP-009067614.

Goerdeler, J., et al.: "Ring-Cleaving Cycloadditions, II, Reaction of Heterocumulenes with 5-Ethoxy-3-phenylimino-3H-1,2,4-dithiazole," *Chem Ber.*, vol. 109, 1976, pp. 848-854, XP-009067616.

Goerdeler, J., et al.: "Ring Cleaving Cycloadditions, IV, Reaction of Iminodithiazoles and-isothiazoles with Simple Heterocumulenes," *Chem. Ber.*, vol. 110, 1977, pp. 285-294, XP-009067618.

Iwataki, I., et al.: "Studies of Dithiobiurets. II. The Thermal Decomposition of 1,1-Dimethyl-5-acetyl-2,4-dithiobiuret," *Bulletin of the Chemical Society of Japan*, vol. 45, No. 10, 1972, pp. 3220-3222, XP-009067613.

Iwataki, I.: "Studies of Dithiobiurets. III. The Preparation and Properties of 3,5-Disubstituted 3H-1,2,4-Dithiazoles," *Bulletin of the Chemical Society of Japan*, vol. 45, No. 12, 1972, pp. 3572-3579, XP-009067612.

Joshua, Chittoor P., et al., "Synthesis of 1,3,5-Trisubstituted 2,4-Dithiobiurets: Their Conversion into 4-Alkyl-3,5di(substituted imino)-1,2,4-dithiazolidines and to Related Benzothiazolylthioureas," Aust. *J. Chem*, Jun. 1982, vol. 35, No. 2, pp. 405-409.

L'Abbé, G., et al.: "5-Imino-1,2,4-Thiadiazolidine-3-Ones as Masked 1,3-Dipoles," *Bull. Soc. Chim. Belg.*, vol. 100, No. 2, 1991, pp. 185-186, XP-009067574.

L'Abbé, G., et al.: "Isomerizations of 1,2,4-Thiadiazolidines Via Thiapentalene Intermediates," *Bull. Soc. Chim. Belg.*, vol. 99, No. 6, 1990, pp. 391-392, XP-009067601.

Linden, H. W., et al.: "Reaktion von Iminodithiazolen mit Sulfenen zu 5-gliedrigen Sultamen," *Tetrahedron Letters*, No. 20, 1977, pp. 1729-1732, XP-002384601.

Oliver, J. E.: "The Reaction of Dithiazolium Cations with Sodium Azide," *J. Org. Chem.*, vol. 4936, No. 22, 1971, pp. 3465-3467, XP-002384599.

Oliver, J. E., et al.: "Imino-1,2,4-dithiazoles. I. Alkylation," *J. Org. Chem.*, vol. 39, No. 15, 1974, pp. 2225-2228, XP-002384600.

Oliver, J. E.: "Imino-1,2,4-dithiazoles. IV. Alkylation as a Probe of No-Bond Resonance," *J. Org. Chem.*, vol. 39, No. 15, 1974, pp. 2235-2239, XP-002384602.

Oliver, J. E., et al.: "5-(Dialkylamino)-1,2,4-dithiazole-3-thiones and 3,5-Disubstituted-1,2,4-dithiazolium Salts," *J. Heterocycl. Chem.*, vol. 9, 1972, pp. 447-449, XP-002384612.

Oliver, J. E., et al.: "Imino-1,2,4-dithiazoles. III. Thermal Decomposition of 5-(Dialkylamino)-3-(substituted imino)-1,2,4-dithiazoles," *J. Org. Chem.*, vol. 39, No. 15, 1974, pp. 2233-2235, XP-002384603.

Oliver, J. E., et al.: "Imino-1,2,4-dithiazoles. II. Dipolar Additions," *J. Org. Chem.*, vol. 39, No. 15, 1974, pp. 2228-2233, XP-002384604.

Pandeya, S. N., et al.: "Synthesis and Biological Activity of Isodithiobiurets, Dithiobiurets, and Dithiazoles," *Pharmaceutical Research*, vol. 4, No. 4, 1987, pp. 321-326, XP-009067578.

Pandeya, S. N., et al.: "Synthesis, Anticonvulsant and Analgesic Activity of 1,2,4-Dithiazoline Derivatives," *Indian Journal of Pharmaceutical Sciences*, Mar.-Apr. 1982, pp. 31-33, XP-009067579.

Siddiqui, N., et al., "Anticonvulsant and Hypnotic Activities of Isodithiobiurets and 1,2,4-Dithiazolines," *Indian Journal of Pharmacology*, 1992, pp. 171-173, XP-009067580.

Stelander, B., et al.: "Synthesis and X-ray Analysis of a New Representative of the Class of 3,4-diaza-Trithiapentalenes," *Bull. Soc. Chim. Belg.*, vol. 86, No. 4, 1977, pp. 291-298, XP-009067626.

Database Beilstein Institut zur Förderung der Chemischen Wissenschaften; XP-002390964 Database accession No. 6728135, 6728136, 6728988, 6729911, 6731373, 6732316, 6732490, 6734279, 6734802, 6736059, 6737002, and 673278.

International Search Report and Written Opinion, dated Aug. 8, 2006, for PCT/EP2006/050744.

* cited by examiner

[1,2,4]-DITHIAZOLI(DI)NE DERIVATIVES, INDUCERS OF GLUTHATHIONE-S-TRANSFERASE AND NADPH QUINONE OXIDO-REDUCTASE, FOR PROPHYLAXIS AND TREATMENT OF ADVERSE CONDITIONS ASSOCIATED WITH CYTOTOXICITY IN GENERAL AND APOPTOSIS IN PARTICULAR

This application claims the benefit of priority of U.S. Provisional Application No. 60/651,661, filed on Feb. 11, 2005, and International Application PCT 2006050744, filed on Feb. 8, 2006, entitled "[1,2,4]-Dithiazoli(di)ne Derivatives, Inducers of Gluthathione-S-Transferase and NADPH Quinone Oxido-Reductase, For Prophylaxis and Treatment of Adverse Conditions Associated With Cytotoxicity in General and Apoptosis in Particular," the full contents of both of which are incorporated herein by reference.

The present invention relates to 5-imino-5H-[1,2,4]-dithiazol-3-yl-amine and [1,2,4]-dithiazolidine-3,5-diylidene-diamine derivatives as inducers of gluthathione-S-transferase (GST) and NADPH quinone oxidoreductase (NQO), to methods for the preparation of these compounds and to novel intermediates useful for the synthesis of said [1,2,4]-dithiazoli(di)ne derivatives. The invention also relates to the use of a compound disclosed herein for the manufacture of a medicament giving a beneficial effect. A beneficial effect is disclosed herein or apparent to a person skilled in the art from the specification and general knowledge in the art. The invention also relates to the use of a compound of the invention for the manufacture of a medicament for treating or preventing a disease or condition. More particularly, the invention relates to a new use for the treatment of a disease or condition disclosed herein or apparent to a person skilled in the art from the specification and general knowledge in the art. In embodiments of the invention specific compounds disclosed herein are used for the manufacture of a medicament useful for prophylaxis and treatment of adverse conditions associated with cytotoxicity in general and apoptosis in particular.

Apoptosis is closely involved in morphogenesis and histogenesis in the development process, maintenance of homeostasis, and bio-defense, and in cell death having an important role in maintaining individual lives. When the death process regulated by genes is congenitally or postnatally hindered, apoptosis is excessively induced or inhibited to cause functional disorders in various organs, and thus diseases. Drugs showing an apoptosis inhibitory activity can be used as agents for the prophylaxis and treatment of diseases which are thought to be mediated by promotion of apoptosis.

The goal of the present invention was to develop antiapoptotic compounds with mechanisms of action different from any of those known in the art.

Surprisingly it was found that [1,2,4]-dithiazoli(di)ne derivatives are inducers of gluthathione-S-transferase (GST), NADPH quinone oxidoreductase (NQO), and other enzymes under control of the "antioxidant responsive element" (ARE). Upregulation of the activity of these enzymes may have beneficial effects in the treatment of neurodegenerative diseases and other diseases where free radical mediated cell degeneration and/or cell death plays a decisive role.

The invention relates to compounds of the general formula (I):

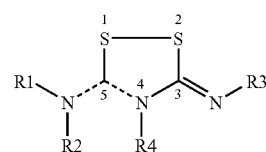

wherein
the dotted lines between carbon atom number 5 and its neighbouring nitrogen atoms represent single or double bonds, with the proviso that one of the two bonds is a single bond and one is a double bond, and the proviso that when the double bond is between carbon atom number 5 and nitrogen atom number 4, R4 is not present and when the double bond is between carbon atom number 5 and the exo-nitrogen atom, R2 is not present,
R1, R2, R3 and R4 independently represent a branched or unbranched alkyl($C_{1-4}$) group, optionally containing sulfur atoms or sulfoxide, amide, ketone, thioketone or sulfone groups, and optionally substituted with halogen, cyano, mono- or dialkyl($C_{1-4}$)amino, trifluoromethyl, ($C_{1-4}$)alkoxy or hydroxyl; or R1 and R2 together with the nitrogen atom to which they are attached, form a 4 to 8 membered ring system in which other (substituted) hetero atoms chosen from N, O and S may be present, and which ring system may be optionally substituted with branched or unbranched alkyl($C_{1-4}$), halogen, cyano, mono- or dialkyl($C_{1-4}$)amino, trifluoromethyl, ($C_{1-4}$)alkoxy or hydroxyl or which ring system contains amide, ketone, thioketone, sulfone or sulfoxide functions; R3 represents hydrogen, a branched or unbranched alkyl($C_{1-4}$) group, optionally containing sulfur atoms or sulfoxide, amide, ketone, thioketone or sulfone groups, and optionally substituted with halogen, cyano, mono- or dialkyl($C_{1-4}$) amino, trifluoromethyl, ($C_{1-4}$)alkoxy, S-alkyl($C_{1-4}$), SH or hydroxyl, or R3 represents an aryl group, optionally substituted with branched or unbranched alkyl($C_{1-4}$), aryl, alkyl ($C_{1-4}$)aryl, SH, S-alkyl($C_{1-4}$), halogen, cyano, mono- or dialkyl($C_{1-4}$)amino, $CF_3$, $OCF_3$, $SCF_3$, nitro, hydroxy or ($C_{1-4}$)alkoxy groups, and tautomers, stereoisomers and N-oxides thereof, as well as pharmacologically acceptable salts, hydrates and solvates of said compounds of formula (I) and its tautomers, stereoisomers and N-oxides.

These compounds are new and are inducers of gluthathione-S-transferase (GST), NADPH quinone oxidoreductase (NQO).

The invention relates to racemates, mixtures of diastereomers as well as the individual stereoisomers of the compounds having formula (I). In the description of the substituents the abbreviation 'alkyl($C_{1-4}$)' means methyl, ethyl, n-propyl, isopropyl, n-butyl, 2-butyl, isobutyl or 2-methyl-n-propyl; the abbreviation 'aryl' means furyl, thienyl, pyrrolyl, oxazolyl, thiazolyl, imidazolyl, pyrazolyl, isoxazolyl, isothiazolyl, pyridyl, pyridazinyl, pyrimidinyl, pyrazinyl, 1,3,5-triazynyl, phenyl, indazolyl, indolyl, indolizinyl, isoindolyl, benzi[b]furanyl, benzo[b]thiophenyl, benzimidazolyl, benzthiazolyl, purinyl, quinolynyl, isochinolyl, chinolyl, phtalazinyl, quinazolinyl, quinoxalinyl, 1,8-naphthyridinyl, pteridinyl, naphthyl or azulenyl, preferably phenyl, pyridyl or naphthyl; the abbreviation 'optionally substituted' means that a group may or may not be further substituted by one or more groups as indicated.

Prodrugs of the compounds mentioned above are in the scope of the present invention. Prodrugs are therapeutic agents which are inactive per se but are transformed into one or more active metabolites. Prodrugs are bioreversible derivatives of drug molecules used to overcome some barriers to the utility of the parent drug molecule. These barriers include, but are not limited to, solubility, permeability, stability, presystemic metabolism and targeting limitations (Medicinal Chemistry: Principles and Practice, 1994, ISBN 0-85186-494-5, Ed.: F. D. King, p. 215; J. Stella, "Prodrugs as therapeutics", Expert Opin. Ther. Patents, 14(3), 277-280, 2004; P. Ettmayer et al., "Lessons learned from marketed and investigational prodrugs", J. Med. Chem., 47, 2393-2404, 2004). Pro-drugs, i.e. compounds which when administered to humans by any known route, are metabolised to compounds having formula (1), belong to the invention. In particular this relates to compounds with primary or secondary amino or hydroxy groups. Such compounds can be reacted with organic acids to yield compounds having formula (1) wherein an additional group is present which is easily removed after administration, for instance, but not limited to amidine, enamine, a Mannich base, a hydroxyl-methylene derivative, an O-(acyloxymethylene carbamate) derivative, carbamate, ester, amide or enaminone.

N-oxides of the compounds mentioned above are in the scope of the present invention. Tertiary amines may or may not give rise to N-oxide metabolites. The extent to which N-oxidation takes place varies from trace amounts to a near quantitative conversion. N-oxides may be more active than their corresponding tertiary amines or less active. While N-oxides are easily reduced to their corresponding tertiary amines by chemical means, in the human body this happens to varying degrees. Some N-oxides undergo nearly quantitative reductive conversion to the corresponding tertiary amines, in other cases the conversion is a mere trace reaction or even completely absent. (M. H. Bickel: "The pharmacology and Biochemistry of N-oxides", Pharmacological Reviews, 21(4), 325-355, 1969).

The invention particularly relates to compounds of the general formula ($I^a$):

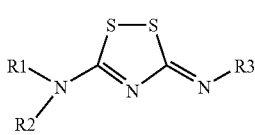

wherein

R1 and R2 independently represent a branched or unbranched alkyl($C_{1-4}$) group, optionally containing sulfur atoms or sulfoxide, amide, kefone, thioketone or sulfone groups, and optionally substituted with halogen, cyano, mono- or dialkyl($C_{1-4}$)amino, trifluoromethyl, ($C_{1-4}$)alkoxy or hydroxyl, or R1 and R2 together with the nitrogen atom to which they are attached, form a 4 to 8 membered ring system in which other (substituted) hetero atoms chosen from N, O and S may be present, and which ring system may be optionally substituted with branched or unbranched alkyl($C_{1-4}$), halogen, cyano, mono- or dialkyl($C_{1-4}$)amino, trifluoromethyl, ($C_{1-4}$)alkoxy or hydroxyl or which ring system contains amide, ketone, thioketone, sulfone or sulfoxide functions; R3 represents hydrogen, a branched or unbranched alkyl($C_{1-4}$) group, optionally containing sulfur atoms or sulfoxide, amide, ketone, thioketone or sulfone groups, and optionally substituted with halogen, cyano, mono- or dialkyl($C_{1-4}$) amino, trifluoromethyl, ($C_{1-4}$)alkoxy, S-alkyl($C_{1-4}$), SH or hydroxyl; or R3 represents an aryl group, optionally substituted with branched or unbranched alkyl($C_{1-4}$), aryl, alkyl ($C_{1-4}$)aryl, SH, S-alkyl($C_{1-4}$), halogen, cyano, mono- or dialkyl($C_{1-4}$)amino, $CF_3$, $OCF_3$, $SCF_3$, nitro, hydroxy or ($C_{1-4}$)alkoxy groups.

More in particular the invention relates to compounds of the general formula ($I^a$) in which:

R1 and R2 independently represent branched or unbranched alkyl($C_{1-4}$) group, or R1 and R2 together with the nitrogen atom to which they are attached, form a 5 to 6 membered ring system in which an oxygen atoms may be present, and which ring system may be optionally substituted with branched or unbranched alkyl($C_{1-4}$), R3 represents an aryl group, optionally substituted with branched or unbranched alkyl($C_{1-4}$), aryl, alkyl($C_{1-4}$)aryl, SH, S-alkyl ($C_{1-4}$), halogen, cyano, mono- or dialkyl($C_{1-4}$)amino, $CF_3$, $OCF_3$, $SCF_3$, nitro, hydroxy or ($C_{1-4}$)alkoxy groups.

Even more particular the invention relates to compounds of the general formula ($I^a$) in which:

R1 and R2 independently represent a methyl group, or R1 and R2 together with the nitrogen atom to which they are attached, form a 5 to 6 membered ring system in which one oxygen atom may be present, and which ring system may be optionally substituted with a methyl group, R3 represents a phenyl or pyridyl group, optionally substituted with branched or unbranched alkyl($C_{1-4}$), benzyl, SH, $SCH_3$, halogen, cyano, $CF_3$, $OCF_3$, $SCF_3$, nitro, hydroxy or methoxy groups.

Also in particular the invention relates to compounds of the general formula ($I^b$)

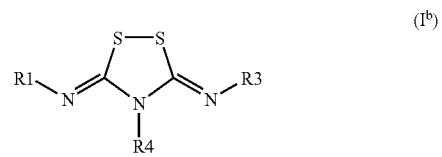

wherein

R1, R3 and R4 independently represent a branched or unbranched alkyl($C_{1-4}$) group, optionally containing sulfur atoms or sulfoxide, amide, ketone, thioketone or sulfone groups, and optionally substituted with halogen, cyano, mono- or dialkyl($C_{1-4}$)amino, trifluoromethyl, ($C_{1-4}$)alkoxy or hydroxyl, or an aryl group, optionally substituted with branched or unbranched alkyl($C_{1-4}$), aryl, alkyl($C_{1-4}$)aryl, SH, S-alkyl($C_{1-4}$), halogen, cyano, mono- or dialkyl($C_{1-4}$) amino, $CF_3$, $OCF_3$, $SCF_3$, nitro, hydroxy or ($C_{1-4}$)alkoxy groups, And more in particular the invention relates to compounds of the general formula ($I^b$) in which:

R1, R3 and R4 independently represent branched or unbranched alkyl($C_{1-4}$) group, or an aryl group, optionally substituted with branched or unbranched alkyl($C_{1-4}$), aryl, alkyl($C_{1-4}$)aryl, halogen, $CF_3$, $OCF_3$, $SCF_3$, nitro, hydroxy or methoxy groups, Even more particular the invention relates to compounds of the general formula ($I^b$) in which:

R1, R3 and R4 independently represent a methyl group or a phenyl group, optionally substituted with branched or unbranched alkyl($C_{1-4}$), halogen, $CF_3$, $OCF_3$, hydroxy or methoxy groups.

General Aspects of Syntheses

Compounds with the general formulae ($I^a$) or ($I^b$) can be obtained according to three methods (schemes A.1, B.1 and C.1):

scheme A.1

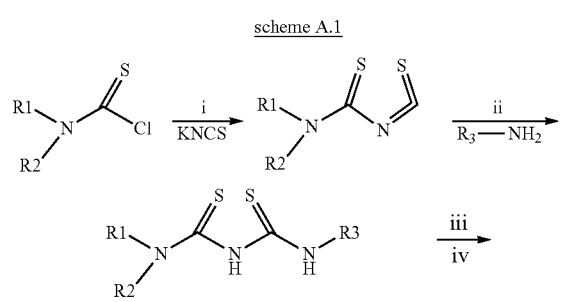

scheme B.1

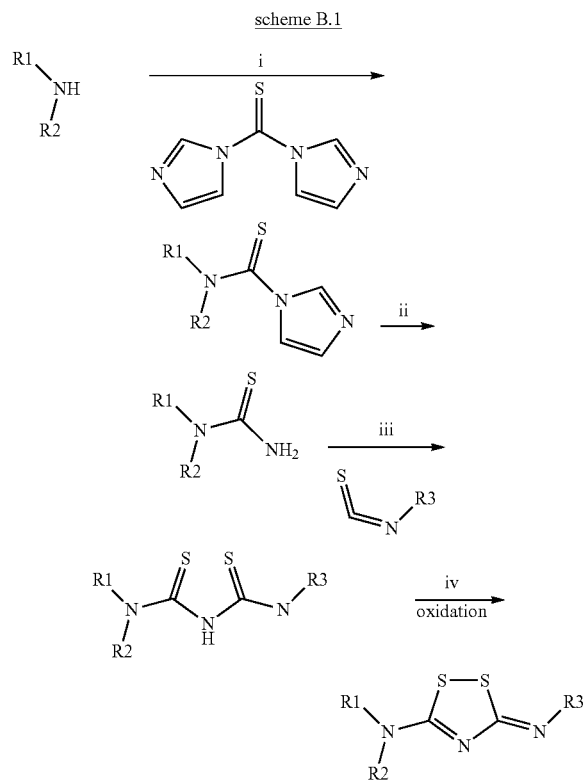

scheme C.1

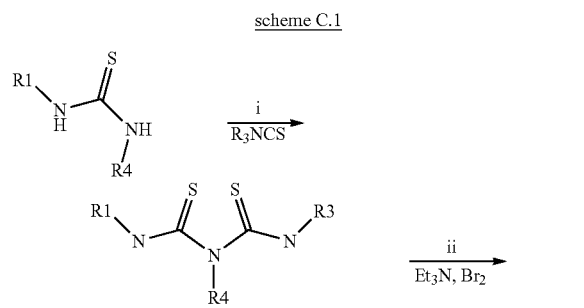

-continued

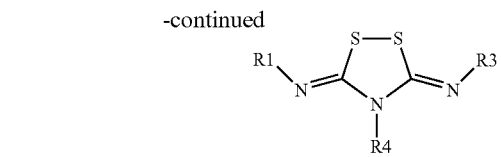

The selection of the particular synthetic procedures depends on factors known to those skilled in the art such as the compatibility of functional groups with the reagents used, the possibility to use protecting groups, catalysts, activating and coupling reagents and the ultimate structural features present in the final compound being prepared.

Pharmaceutically acceptable salts may be obtained using standard procedures well known in the art, for example by mixing a compound of the present invention with a suitable acid, for instance an inorganic acid such as hydrochloric acid, or with an organic acid.

The compounds of the invention of the general formula (I), as well as the salts thereof, are inducers of gluthathione-S-transferase (GST), NADPH quinone oxidoreductase (NQO), and other enzymes under control of the "antioxidant responsive element" (ARE). Upregulation of the activity of these enzymes may have beneficial effects in the treatment of neurodegenerative diseases and other diseases. where free radical mediated cell degeneration and/or cell death (apoptosis) plays a decisive role. The compounds of the invention are active at doses in the range of 0.1-100 mg/kg after oral administration, and are useful in prophylaxis and treatment of adverse conditions associated with apoptosis. Said conditions are for instance: neurodegenerative disorders such as e.g. ischemic stroke, traumatic brain injury, acute disseminated encephalomyelitis, amyotrophic lateral sclerosis (ALS), retinitis pigmentosa, mild cognitive impairment, Alzheimer's disease, Pick's disease, senile dementia, progressive supranuclear palsy, subcortical dementias, Wilson disease, multiple infarct disease, arteriosclerotic dementia, AIDS associated dementia, cerebellar degeneration, spinocerebellar degeneration syndromes, Friedreichs ataxia, ataxia telangiectasia, epilepsy related brain damage, spinal cord injury, restless legs syndrome, Huntington's disease and Parkinson's disease, striatonigral degeneration, cerebral vasculitis, mitochondrial encephalomyopathies, neuronal ceroid lipofuscinosis, spinal muscular atrophies, lysosomal storage disorders with central nervous system involvement, leukodystrophies, urea cycle defect disorders, hepatic encephalopathies, renal encephalopathies, metabolic encephalopathies, porphyria, bacterial or viral meningitis and meningoencephalitis, prion diseases, poisonings with neurotoxic compounds, Guillain Barre syndrome, chronic inflammatory neuropathies, polymyositis, dermatomyositis, radiation-induced brain damage; irritable bowel disease and inflammatory bowel diseases, Crohn's disease and ulcerative colitis, coeliac disease, *Helicobacter pylori* gastritis and other infectious gastritides, necrotizing enterocolitis, pseudomembranous enterocolitis, radiation-induced enterocolitis, lymphocytic gastritis, graft-versus-host disease, acute and chronic pancreatitis; hepatic diseases such as e.g. alcoholic hepatitis, viral hepatitis, metabolic hepatitis, autoimmune hepatitis, radiation-induced hepatitis, liver cirrhosis, hemolytic uremic syndrome, glomerulonephritis, lupus nephritis, viral diseases such fulminant hepatitis: joint-diseases such as trauma and osteoarthritis; immuno-suppression or immunodeficiency, in particular autoimmune diseases like idiopathic inflammatory myopathy, chronic neutropenia, thrombotic thrombocytopenic purpura, rheumatoid arthritis, idiopathic thrombocytopenic purpura, autoimmune haemolytic syndromes, antiphospholipid antibody syndromes, myocarditis, multiple sclerosis and its diagnostic sub-classifications relapsing-remitting multiple sclerosis, secondary progressive multiple sclerosis, primary progressive multiple sclerosis, progressive relapsing multiple sclerosis, acute multiple sclerosis, benign relapsing multiple sclerosis or asymptomatic multiple sclerosis, neuromyelitis optica (Devic's syndrome), lymphocytic hypophysitis, Grave's disease, Addison's disease, hypoparathyroidism, type 1 diabetes, systemic lupus erythematodes, pemphigus vulgaris, bullous pemphigoid, psoriatic arthritis, endometriosis, autoimmune orchitis, autoimmune erectile dysfunction, sarcoidosis, Wegener's granulomatosis, autoimmune deafness, Sjögren's disease, autoimmune uveoretinitis, interstitial cystitis, Goodpasture's syndrome and fibromyalgia; myelodysplasias such as aplastic anemia; dermatological diseases including pemphigous vulgaris, dermatomyositis, atopic dermatitis, Henoch-Schonlein purpura, acne, systemic sclerosis, seborrhoeic keratosis, cutaneous mastocytosis, chronic proliferative dermatitis, dyskeratosis, scleroderma, interstitial granulomatous dermatitis, psoriasis, bacterial infections of the skin, dermatomycoses, lepra, cutaneous leishmaniasis, vitiligo, toxic epidermal necrolysis, Steven Johnson syndrome, sebaceous adenoma, alopecia, photodamage of the skin, lichen sclerosus, acute cutaneous wounds, incontinentia pigmenti, thermal damage of the skin, exanthematous pustulosis, lichenoid dermatosis, cutaneous allergic vasculitis, cytotoxic dermatitis; diseases of the inner ear such as e.g. acoustic trauma-induced auditory hair cell death and hearing loss, aminoglycoside induced auditory hair cell death and hearing loss, ototoxic drug-induced hearing loss, perilymphatic fistula, cholesteatoma, cochlear or vestibular ischemia, Meniere's disease, radiation-induced hearing loss, hearing loss induced by bacterial or viral infections and idiopathic hearing loss; transplantation: graft-versus-host disease, acute and chronic rejection of heart-, lung-, kidney-, skin-corneal-, bone marrow- or liver-transplants; wound healing and tissue rejection.

Pharmaceutical Preparations

The compounds of the invention can be brought into forms suitable for administration by means of usual processes using auxiliary substances such as liquid or solid carrier material. The pharmaceutical compositions of the invention may be administered enterally, orally, parenterally (intramuscularly or intravenously), rectally or locally (topically). They can be administered in the form of solutions, powders, tablets, capsules (including microcapsules), ointments (creams or gel) or suppositories. Suitable excipients for such formulations are the pharmaceutically customary liquid or solid fillers and extenders, solvents, emulsifiers; lubricants, flavorings, colorings and/or buffer substances. Frequently used auxiliary substances which may be mentioned are magnesium carbonate, titanium dioxide, lactose, mannitol and other sugars or sugar alcohols, talc, lactoprotein, gelatin, starch, cellulose and its derivatives, animal and vegetable oils such as fish liver oil, sunflower, groundnut or sesame oil, polyethylene glycol and solvents such as, for example, sterile water and mono- or polyhydric alcohols such as glycerol.

Compounds of the present invention are generally administered as pharmaceutical compositions which are important and novel embodiments of the invention because of the presence of the compounds, more particularly specific compounds disclosed herein. Types of pharmaceutical compositions that may be used include but are not limited to tablets, chewable tablets, capsules, solutions, parenteral solutions, suppositories, suspensions, and other types disclosed herein or apparent to a person skilled in the art from the specification and general knowledge in the art. In embodiments of the invention, a pharmaceutical pack or kit is provided comprising one or more containers filled with one or more of the ingredients of a pharmaceutical composition of the invention. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration.

Pharmacological Methods

Spectrophotometric Determination of EC 2.5.1.18 (GST) Induction

Rat PC-12 cells are incubated for 24 hours with a test compound. GST activity is measured using 1-chloro-2,4-dinitrobenzene (CDNB) and gluthathine (GSH) as substrates. The enzyme catalyses the reaction converting these substrates into S-(2,4-dinitrophenyl)glutathione, which product is measured spectrophotometrically at 340 nm. The effect of the test compound is expressed as $pEC_{50}$: the negative logarithm of the molar concentration of the compound which causes 50% induction of the enzyme activity. Also the maximal percentage enzyme induction is determined. (see Drukarch et al. "*Anethole dithiolethione prevents oxidative damage in gluthathione-depleted astrocytes*", *Eur. J. Pharmacol.* 329, 259-262, 1997).

Spectrophotometric Determination of EC 1.6.99.2 (NQO) Induction

Rat PC-12 cells are incubated for 24 hours with a test compound. NAD(P)H: oxidoreductase (NQO, EC 1.6.99.2) activity is measured using menadione as substrate and MTT as readout compound. The formation of formazan from MTT is measured spectrophotometrically at 540 nm. The percentage stimulation (PS) relative to the maximal effect of the reference compound D3T is calculated. The maximal percentage stimulation with the concentration which induced the maximal percentage as condition and the $pEA_{50}$ value (the negative logarithm of the molar concentration of the compound which caused the same half maximal induction of the enzyme activity as the reference compound D3T) are recorded (see Murphy et al., "*Enhanced NAD(P)H:Quinone reductase activity defenses in neuronal cells prevents free radical-mediated damage*", *J. Neurochem.*, 71 69-77, 1998 and Prochaska et al., *Analytical Biochemistiy*, 169, 328-336 1988).

Dose

The potency of the compounds of the invention as inducers of gluthathione-S-transferase (GST), NADPH quinone oxidoreductase (NQO), was determined as described above. From the potency measured for a given compound of formula (I), one can estimate a theoretical lowest effective dose. At a concentration of the compound equal to twice the measured $EC_{50}$ the enzyme activity is likely to be doubled. Converting that concentration to mg of compound per kg of patient yields a theoretical lowest effective dose, assuming ideal bioavailability. Pharmacokinetic, pharmacodynamic, and other considerations may alter the dose actually administered to a higher or lower value. The dosage expediently administered is 0.001-1000 mg/kg, preferably 0.1-100 mg/kg of patient's bodyweight.

Treatment

The term "treatment" as used herein refers to any treatment of a mammalian, preferably human condition or disease, and includes: (1) preventing the disease or condition from occurring in a subject which may be predisposed to the disease but has not yet been diagnosed as having it, (2) inhibiting the disease or condition, i.e., arresting its development, (3) relieving the disease or condition, i.e., causing regression of the condition, or (4) relieving the conditions caused by the disease, i.e., stopping the symptoms of the disease.

EXAMPLES

Example 1

Materials and Methods

All reactions involving moisture sensitive compounds were carried out under a dry nitrogen atmosphere. All other commercially available chemicals were used without further purification. Reactions were monitored by using thin-layer chromatography (TLC) on silica coated plastic sheets (Merck silica gel 60 F254) with the indicated eluent. The compounds were visualised by UV light (254 nm) or $I_2$. Flash chromatography refers to purification using the indicated eluent and Acros silica gel (0.030-0.075 mm). Nuclear magnetic resonance spectra ($^1$H NMR) were determined in the indicated solvent. Coupling constants J are given in Hz. Peakshapes in the NMR spectra are indicated with the symbols 'q' (quartet), 'dq' (double quartet), 't' (triplet), 'dt' (double triplet), 'd' (doublet), 'dd' (double doublet), 's' (singlet), 'bs' (broad singlet) and 'm' (multiplet).

Example 2

Syntheses of Specific Compounds

Synthesis Route A:
The used thiocarbamoylchlorides are either commercially available or accessible via methods described in Gördeler et al., *Chem. Ber.*, 103(1970)3393 and von Braun et al., *Berichte Deutsche Chem. Ges.*, 36(1903)2274

Compound A2:

Procedure A (Scheme A.1) Steps i+ii:
12.3 grams (99 mmol) of N,N-dimethylthiocarbamoyl chloride were dissolved in 60 ml of acetonitrile; While stirring, a solution of 9.9 grams (99 mmol) of potassium isothiocyanate (KSCN) in 180 ml of acetonitrile, was added to the reaction mixture. Then the mixture was heated to reflux temperature, after which refluxing was continued for three minutes. Subsequently the reaction mixture was added to a stirred solution of 13.5 grams (90 mmol) 4-n-butylaniline in 100 ml of acetonitrile. The latter mixture was stirred for a short time after which the solvent was removed in vacuo. Water was added on which the residual oil turned into a solid. The solid/water mixture was made into a suspension after which it was filtered. The residue was washed with water, subsequently with a little isopropanol after which it was allowed to dry. Yield of crude product: 24.4 gram (92%). Recrystallization from isopropanol (ca. 200 ml) yielded 16.7 grams (63%) of the corresponding dithiobiuret, m.p. 89.5-91° C. $^1$H NMR (90 MHz, d$^6$-DMSO) δ (ppm): 0.93 (t, 3H), 1.15-2.05 (m, 4H), 2.61 (t, 3H), 3.35 (s, 6H), 7.18 (d, 2H), 7.55 (d, 2H), 9.79 (s, 2H).

Procedure A1 (Scheme A1) Steps iii+iv:
11.8 grams (40 mmol) of the previously prepared dithiobiuret was solved in 300 ml of alcohol. While stirring, a solution containing 13.5 grams of iodine (53.2 mmol) and 16.7 potassium iodide (100 mmol) in 20 ml of water was added until the iodine color did not disappear anymore. The solution was allowed to stand upon which crystals formed. The mixture was filtered, the residue washed with alcohol, isopropanol and petroleum ether, yielding 13.4 grams (80%) of the mono hydrogen iodide salt. Step iv: 10.5 grams of the latter was suspended in water (250 ml) and, while stirring, 14 ml of 2N KOH was added. After 1.5 hours the suspension was filtered, the residue washed with water, a little isopropanol and petroleum ether, yielding 6.5 grams. The latter amount was recrystallized from 100 ml of ligroin, yielding 3.3 grams (45%) of pure product A2 as a free base. M.p.: 81-82.5° C. $^1$H NMR (90 MHz, CDCl$_3$) δ (ppm): 0.93 (t, 3H), 1.1-1.9 (m, 4H), 2.60 (t, 2H), 3.35 (s, 6H), 6.94 and 7.16 (dd, 4H).

Compound A19:

Procedure A (Scheme A.1) Steps i to iv:
2 grams (16.3 mmol) of dimethylthiocarbamoylchloride and 1.58 grams of KNCS (16.3 mmol) were suspended in acetonitrile and heated to reflux for 2 minutes using a hotgun. To the resulting hot mixture was added 1.97 grams (16.3 mmol) of (2,6)-dimethylaniline in 10 ml of acetonitrile. After 1 hour the mixture was filtered and the filtrate was concentrated. The resulting oil containing the dithiobiuret was dissolved in 40 ml of ethanol and, a solution of 6.7 grams of iodine and 8.4 grams of potassium iodide in 20 ml of water, was added until the solution did not change color. Stirring was continued for 1 hour after which the reaction mixture was filtered, the residue washed with water, 2M KOH and again water. Subsequently the residue was washed with diethyl ether and allowed to dry, yielding 2.2 grams (49%) of the free base A19 as a yellowish solid. M.p.: 236.3-239.2° C. (DSC). $^1$H-NMR (200 MHz, d$^6$-DMSO) δ (ppm): 2.28 (s, 6H), 2.57 (s, 6H), 7.16-7.45 (m, 4H). Mass (Cl): (M$^+$+1): 266.

According to the syntheses given above, the compounds A1-A22 (table A), all with the general formula (1$^a$), were prepared:

| compound | R1 | R2 | R3 | melting point ° C. |
|---|---|---|---|---|
| A1 | Me | Me | Ph | 216 (decomp) |
| A2 | Me | Me | 4-(n-But)-Ph | 81-82.5 |
| A3 | Me | Me | 4-MeO—Ph | 129.5-131.5 |
| A4 | Me | Me | 3-Cl—Ph | 113-114.5 |
| A5 | Me | Me | 2,6-(di-Cl)—Ph | 191.5-193.5 |
| A6 | Me | Me | 3-NO$_2$—Ph | 134.5-136.5 |
| A7 | —(CH$_2$)$_4$— | | Ph | 149-151.5 |
| A8 | —(CH$_2$)$_2$O(CH$_2$)$_2$— | | Ph | 175.5-176.5 |
| A9 | Me | Me | 2-Me—Ph | 138.5-140 |
| A10 | Me | Me | 4-NO$_2$—Ph | 170-171.5 |
| A11 | Me | Me | 4-F—Ph | 137-138.5 |
| A12 | Me | Me | 2-(i-Pr)—Ph | 194.6-197.5 |
| A13 | Me | Me | 2-F—Ph | 126.8-128.2 |
| A14 | Me | Me | 2-MeS—Ph | 119.4-120.3 |
| A15 | Me | Me | 3-Me—Ph | 201-204 |
| A16 | Me | Me | 2-Et—Ph | 177.8-184 |
| A17 | Me | Me | 2-MeO—Ph | 148.5-152 |
| A18 | Me | Me | 2-CF$_3$—Ph | 129.1-130.8 |
| A19 | Me | Me | 2,6-(di-Me)—Ph | 236.3-239.2 |
| A20 | Me | Me | 2-pyridyl | 166-173 |
| A21 | Me | Me | 2-benzyl-Ph | 176-182 |
| A22 | Me | Me | 3-pyridyl | 83-90 |

(in all cases the compounds were prepared as free bases, except for A1 which was prepared as the monohydrogen iodide. Abbreviations used are: Me=methyl; Ph=phenyl; Et=ethyl, But=butyl; i-Pr=iso-propyl;)

Synthesis Route B:

Compound B4:

Procedure B (Scheme B.1) Step i+ii:

10 grams (56 mmol) of thiocarbonyldiimidazole was dissolved in THF (400 ml). 4.78 grams (56 mmol) of piperidine was added and stirred at 50° C. for 3 hours. The mixture was partially concentrated and subsequently mixed with 500 ml 7N $NH_3$ in methanol, after which it was put away in a sealed vessel overnight at 45° C. At room temperature the reaction mixture was partially concentrated after which it was cooled. The precipitate containing the thiourea derivative was collected and dried to give 1.3 g (16%) as a grey solid.

Procedure B (Scheme B.1) Steps iii+iv:

1 gram (6.85 mmol) of the urea derivative of the previous step was dissolved in 40 ml of acetonitrile, after which 500 mg of powdered KOH was added and the mixture was stirred for 30 minutes at room temperature. Subsequently 1.02 grams (6.85 mmol) of 2-methylphenylisothiocyanate was added and the reaction mixture was stirred for 2 hours. The mixture was filtered and the filtrate concentrated. The resulting oil was dissolved; in ethanol (40 ml) and a solution, of 6.7 grams of iodine and 8.4 grams of potassium iodide in 20 ml of water, was added until the solution did not change color. Stirring was continued for 1 hour after which the reaction mixture was filtered, the residue washed with water, 2M KOH and again water. Subsequently the residue was washed with diethyl ether and allowed to dry, yielding 781 milligrams (39%) of the free base B4 as an off white solid. M.p.: 104.3-112.2° C. (DSC). $^1$H-NMR (200 MHz, $d^6$-DMSO) δ (ppm): 1.77 (s, 6H), 2.31 (s, 3H), 3.78 (broad, 4H), 6.95-7.40 (m, 4H). Mass (CI): ($M^+$+1): 292.

According to the synthesis given above, the compounds B1-B16 (table B), all with the general formula (1a) were prepared.

Synthesis Route C:

Compound C10:

Procedure C (Scheme C.1) Step i:

While stirring, 3.4 grams (32.6 mmol) was dissolved in 100 ml of acetonitile, after which 1.3 grams (32.6 mmol) of powdered NaOH were added. Stirring was continued for 3 hours. Then 5 grams (32.6 mmol) of 4-fluorophenylisothiocyanate were added after which the mixture was allowed to react overnight. Water and tert-butyl methyl ether (TBME) were added as well as 5 ml of concentrated hydrochloric acid. After shaking the biphasic mixture, the organic layer was separated and concentrated in vacuo. The residue was taken up in toluene and filtered. An oily substance separated and was removed from the filtrate. The filtrate was concentrated in vacuo, the residue taken up in TBME and 1M NaOH. The aqueous layer was washed with TBME three times. Subsequently, the aqueous layer was acidified with concentrated HCl after which extraction took place with TBME (3×). The combined organic fractions were concentrated in vacuo to yield 2.5 grams (30%) of the dithiobiuret derivative as a yellow solid.

Procedure C1 (Scheme C1) Step ii:

2.5 grams (9.7 mmol) of the dithiobiuret prepared in step i, were dissolved in 80 ml of dichloromethane to which a solution of 0.5 ml (9.8 mmol, d=3.119 g/ml) of bromine in 20 ml of dichloromethane, was added dropwise. The reaction mixture was stirred for 30 minutes and the formed precipitate was filtered. The residue was washed with dichloromethane and TBME and then allowed to dry in vacuo which yielded 1.8 gram of an orange solid. The latter amount was suspended in dichloromethane and treated with 4.21 ml (30 mmol, 3 eq, d=0.72 g/ml) of triethylamine, the whole being stirred for 30 minutes. The reaction mixture was washed with water (3×), after which the organic layer was concentrated in vacuo. The residue was recrystallized twice from ethanol, yielding 275

| cmp | R1 and R2 | R3 | melting point ° C. |
|---|---|---|---|
| B1 | —($CH_2$)$_2$O($CH_2$)$_2$— | 2-Me—Ph | 139-142 |
| B2 | —($CH_2$)$_4$— | 2-Me—Ph | 126.8-128 |
| B3 | —($CH_2$)$_2$NMe($CH_2$)$_2$— | 2-Me—Ph | 134-142 |
| B4 | —($CH_2$)$_5$— | 2-Me—Ph | 104.3-112.2 |
| B5 | —($CH_2$)$_2$O($CH_2$)$_2$— | 3-Me—Ph | 217-226 |
| B6 | —($CH_2$)$_2$O($CH_2$)$_2$— | 2-MeO—Ph | 160-164 |
| B7 | —($CH_2$)$_2$O($CH_2$)$_2$— | 2-F—Ph | 144-149 |
| B8 | —($CH_2$)$_2$O($CH_2$)$_2$— | 2-$CF_3$—Ph | 138-140.5 |
| B9 | —($CH_2$)$_2$O($CH_2$)$_2$— | 2-MeS—Ph | 160-168 |
| B10 | —($CH_2$)$_2$O($CH_2$)$_2$— | 2-Et—Ph | 195.6 |
| B11 | —($CH_2$)$_2$S($CH_2$)$_2$— | 2-Et—Ph | 145.2 |
| B12 | —($CH_2$)$_2$S($CH_2$)$_2$— | 2-F—Ph | 178.7 |
| B13 | —$CH_2$—CH($CH_3$)OCH($CH_3$)—$CH_2$— | 2-Et—Ph | 182.2-188.1 |
| B14 | —$CH_2$—CH($CH_3$)OCH($CH_3$)—$CH_2$— | 2-F—Ph | 199.4-203.9 |
| B15 | —$CH_2$—CH($CH_3$)OCH($CH_3$)—$CH_2$— | 2-MeO—Ph | 193.4-196.5 |
| B16 | —($CH_2$)$_2$O($CH_2$)$_2$— | —($CH_2$)$_3$-(N-pyrrolidinone) | 179.5-183 |

(in all cases the compounds were prepared as free bases)

mg (11%) of yellow product C10. M.p.: 81.2-84.4° C. (DSC).
$^1$H-NMR (200 MHz, CDCl$_3$) δ (ppm): 3.26 (s, 3H), 3.57 (s, 3H), 6.95-7.20 (m, 4H).

According to the syntheses given above, the compounds C1-C11, all with the general formula (I$^b$), (table A) were prepared.

| compound | R1 | R4 | R3 | melting point ° C. |
|---|---|---|---|---|
| C1 | Me | Me | Me | 100-102 |
| C2 | Me | Me | Ph | 80-82 |
| C3 | Me | Me | 2-Me—Ph | 100-101.4 |
| C4 | Me | Me | 4-Me—Ph | 113.2-114.5 |
| C5 | Me | Me | 2-(i-Pr)—Ph | 80.5-82 and 293-296 |
| C6 | Me | Me | 2-MeO—Ph | 85.7-88.6 and 291-296 |
| C7 | Me | Me | 4-MeO—Ph | 54.6-56.2 and 286-295 |
| C8 | Me | Me | 2-Cl—Ph | 92.5-95.3 |
| C9 | Me | Me | 2,6-(di-Cl)—Ph | 82.8-83.8 |
| C10 | Me | Me | 4-F—Ph | 81.2-84.4 |
| C11 | Me | Me | 3-F—Ph | 76.5-77.6 |

(in all cases the compounds were prepared as free bases)

The specific compounds of which the synthesis is described above are intended to further illustrate the invention in more detail, and therefore are not deemed to restrict the scope of the invention in any way. Other embodiments of the invention will be apparent to those skilled in the art from consideration of the specification and practice of the invention disclosed herein. It is thus intended that the specification and examples be considered as exemplary only, with a true scope and spirit of the invention being indicated by the claims.

Example 3

Formulation of Compound A10

For oral (p.o.) administration: to the desired quantity (0.5-5 mg) of the solid compound A10 in a glass tube, some glass beads were added and the solid was milled by vortexing for 2 minutes. After addition of 1 ml of a solution of 1% methylcellulose in water and 2% (v/v) of Poloxamer 188 (Lutrol F68), the compound was suspended by vortexing for 10 minutes. The pH was adjusted to 7 with a few drops of aqueous NaOH (0.1N). Remaining particles in the suspension were further suspended by using an ultrasonic bath.

For intraperitoneal (ip.) administration: to the desired quantity (0.5-15 mg) of the solid compound A10 in a glass tube, some glass beads were added and the solid was milled by vortexing for 2 minutes. After addition of 1 ml of a solution of 1% methylcellulose and 5% mannitol in water, the compound was suspended by vortexing for 10 minutes. Finally the pH was adjusted to 7.

Example 4

Pharmacological Test Results

Some enzyme induction data obtained according to the protocols given above are shown in the table below.

| Compound | ENZYME INDUCTION | |
|---|---|---|
| | GST pEC$_{50}$ | NQO pEA$_{50}$ |
| A2 | 5.2 | 5.2 |
| A10 | 5.4 | 5.8 |
| B5 | 5.3 | 5.7 |
| C2 | 5.8 | 6.2 |
| C3 | 5.8 | 5.7 |
| C11 | 5.6 | 5.3 |

What is claimed is:

1. A compound of formula (I):

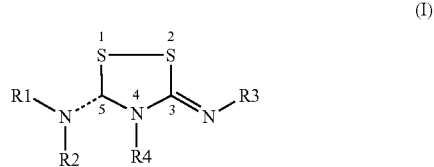

or a tautomer, stereoisomer, or N-oxide thereof, or a pharmacologically acceptable salt of any of the foregoing,
wherein the compound of formula (I) has anti-apoptotic activity, and
wherein the dotted lines represent single or double bonds, and wherein the compound of formula (I) is chosen from the compounds listed below:

| R1 | R2 | R3 | R4 |
|---|---|---|---|
| CH$_3$ | CH$_3$ | 2-pyridyl | — |
| CH$_3$ | CH$_3$ | 2-F-phenyl | — |
| CH$_3$ | CH$_3$ | 2-CH$_3$-phenyl | — |
| CH$_3$ | CH$_3$ | 2-CF$_3$-phenyl | — |
| CH$_3$ | CH$_3$ | 2-CH$_3$CH$_2$-phenyl | — |
| CH$_3$ | CH$_3$ | 2-(i-Pr)-phenyl | — |
| CH$_3$ | CH$_3$ | 2-CH$_3$O-phenyl | — |
| CH$_3$ | CH$_3$ | 2-CH$_3$S-phenyl | — |
| CH$_3$ | CH$_3$ | 2-benzyl-phenyl | — |
| CH$_3$ | CH$_3$ | 2,6-Cl$_2$-phenyl | — |
| CH$_3$ | CH$_3$ | 2,6-(CH$_3$)$_2$-phenyl | — |
| CH$_3$ | CH$_3$ | 3-Cl-phenyl | — |
| CH$_3$ | CH$_3$ | 3-CH$_3$-phenyl | — |
| CH$_3$ | CH$_3$ | 3-NO$_2$-phenyl | — |
| CH$_3$ | CH$_3$ | 4-(n-Bu)-phenyl | — |
| —(CH$_2$)$_4$— | | 2-CH$_3$-phenyl | — |
| —(CH$_2$)$_5$— | | 2-CH$_3$-phenyl | — |
| —(CH$_2$)$_2$O(CH$_2$)$_2$— | | phenyl | — |
| —(CH$_2$)$_2$O(CH$_2$)$_2$— | | 2-F-phenyl | — |
| —(CH$_2$)$_2$O(CH$_2$)$_2$— | | 2-CH$_3$-phenyl | — |
| —(CH$_2$)$_2$O(CH$_2$)$_2$— | | 2-CF$_3$-phenyl | — |
| —(CH$_2$)$_2$O(CH$_2$)$_2$— | | 2-CH$_3$CH$_2$-phenyl | — |
| —(CH$_2$)$_2$O(CH$_2$)$_2$— | | 2-CH$_3$O-phenyl | — |
| —(CH$_2$)$_2$O(CH$_2$)$_2$— | | 2-CH$_3$S-phenyl | — |
| —(CH$_2$)$_2$O(CH$_2$)$_2$— | | 3-CH$_3$-phenyl | — |
| —(CH$_2$)$_2$O(CH$_2$)$_2$— | | 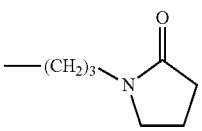 | — |
| —CH$_2$—CH(CH$_3$)OCH(CH$_3$)—CH$_2$— | | 2-F-phenyl | — |
| —CH$_2$—CH(CH$_3$)OCH(CH$_3$)—CH$_2$— | | 2-CH$_3$O-phenyl | — |
| —CH$_2$—CH(CH$_3$)OCH(CH$_3$)—CH$_2$— | | 2-CH$_3$CH$_2$-phenyl | — |
| —(CH$_2$)$_2$S(CH$_2$)$_2$— | | 2-F-phenyl | — |

-continued

| R1 | R2 | R3 | R4 |
|---|---|---|---|
| | —(CH₂)₂S(CH₂)₂— | 2-CH₃CH₂-phenyl | — |
| | —(CH₂)₂N(CH₃)(CH₂)₂— | 2-CH₃-phenyl | — |
| CH₃ | — | Cl | CH₃ |
| CH₃ | — | CH₃ | CH₃ |
| CH₃ | — | 2-(i-Pr)-phenyl | CH₃ |
| CH₃ | — | 2-CH₃O-phenyl | CH₃ |
| CH₃ | — | 2,6-Cl₂-phenyl | CH₃ |
| CH₃ | — | 3-F-phenyl | CH₃ |
| CH₃ | — | 4-F-phenyl | CH₃. |

2. A pharmaceutical composition comprising, at least one pharmaceutically acceptable carrier and/or at least one pharmaceutically acceptable auxiliary substance, and a pharmacologically active amount of at least one compound of formula (I):

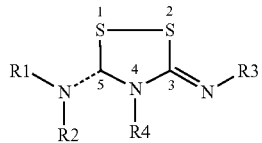

(I)

or a tautomer, stereoisomer, or N-oxide thereof, or a pharmacologically acceptable salt of any of the foregoing, wherein the compound of formula (I) has anti-apoptotic activity, and wherein the dotted lines represent single or double bonds, and wherein the compound of formula (I) is chosen from the compounds listed below:

| R1 | R2 | R3 | R4 |
|---|---|---|---|
| CH₃ | CH₃ | 2-pyridyl | — |
| CH₃ | CH₃ | 3-pyridyl | — |
| CH₃ | CH₃ | 2-F-phenyl | — |
| CH₃ | CH₃ | 2-CH₃-phenyl | — |
| CH₃ | CH₃ | 2-CF₃-phenyl | — |
| CH₃ | CH₃ | 2-CH₃CH₂-phenyl | — |
| CH₃ | CH₃ | 2-(i-Pr)-phenyl | — |
| CH₃ | CH₃ | 2-CH₃O-phenyl | — |
| CH₃ | CH₃ | 2-CH₃S-phenyl | — |
| CH₃ | CH₃ | 2-benzyl-phenyl | — |
| CH₃ | CH₃ | 2,6-Cl₂-phenyl | — |
| CH₃ | CH₃ | 2,6-(CH₃)₂-phenyl | — |
| CH₃ | CH₃ | 3-Cl-phenyl | — |
| CH₃ | CH₃ | 3-CH₃-phenyl | — |
| CH₃ | CH₃ | 3-NO₂-phenyl | — |
| CH₃ | CH₃ | 4-F-phenyl | — |
| CH₃ | CH₃ | 4-CH₃O-phenyl | — |
| CH₃ | CH₃ | 4-(n-Bu)-phenyl | — |
| | —(CH₂)₄— | 2-CH₃-phenyl | — |
| | —(CH₂)₄— | 2-CH₃-phenyl | — |
| | —(CH₂)₅— | 2-CH₃-phenyl | — |
| | —(CH₂)₂O(CH₂)₂— | phenyl | — |
| | —(CH₂)₂O(CH₂)₂— | 2-F-phenyl | — |
| | —(CH₂)₂O(CH₂)₂— | 2-CH₃-phenyl | — |
| | —(CH₂)₂O(CH₂)₂— | 2-CF₃-phenyl | — |
| | —(CH₂)₂O(CH₂)₂— | 2-CH₃CH₂-phenyl | — |
| | —(CH₂)₂O(CH₂)₂— | 2-CH₃O-phenyl | — |
| | —(CH₂)₂O(CH₂)₂— | 2-CH₃S-phenyl | — |
| | —(CH₂)₂O(CH₂)₂— | 3-CH₃-phenyl | — |

-continued

| R1 | R2 | R3 | R4 |
|---|---|---|---|
| | —(CH₂)₂O(CH₂)₂— | 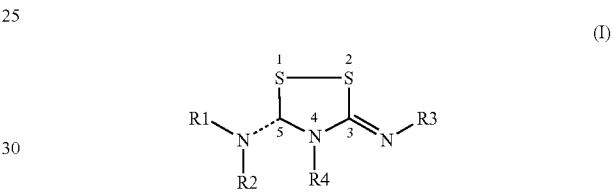 | — |
| | —CH₂—CH(CH₃)OCH(CH₃)—CH₂— | 2-F-phenyl | — |
| | —CH₂—CH(CH₃)OCH(CH₃)—CH₂— | 2-CH₃O-phenyl | — |
| | —CH₂—CH(CH₃)OCH(CH₃)—CH₂— | 2-CH₃CH₂-phenyl | — |
| | —(CH₂)₂S(CH₂)₂— | 2-F-phenyl | — |
| | —(CH₂)₂S(CH₂)₂— | 2-CH₃CH₂-phenyl | — |
| | —(CH₂)₂N(CH₃)(CH₂)₂— | 2-CH₃-phenyl | — |
| CH₃ | — | Cl | CH₃ |
| CH₃ | — | CH₃ | CH₃ |
| CH₃ | — | 2-(i-Pr)-phenyl | CH₃ |
| CH₃ | — | 2-CH₃O-phenyl | CH₃ |
| CH₃ | — | 2,6-Cl₂-phenyl | CH₃ |
| CH₃ | — | 3-F-phenyl | CH₃ |
| CH₃ | — | 4-F-phenyl | CH₃. |

3. A medicament comprising a compound of formula (I)

(I)

or a tautomer, stereoisomer, or N-oxide thereof, or a pharmacologically acceptable salt of any of the foregoing, wherein the compound of formula (I) has anti-apoptotic activity, and wherein the dotted lines represent single or double bonds, and wherein the compound of formula (I) is chosen from the compounds listed below:

| R1 | R2 | R3 | R4 |
|---|---|---|---|
| CH₃ | CH₃ | 2-pyridyl | — |
| CH₃ | CH₃ | 3-pyridyl | — |
| CH₃ | CH₃ | 2-F-phenyl | — |
| CH₃ | CH₃ | 2-CH₃-phenyl | — |
| CH₃ | CH₃ | 2-CF₃-phenyl | — |
| CH₃ | CH₃ | 2-CH₃CH₂-phenyl | — |
| CH₃ | CH₃ | 2-(i-Pr)-phenyl | — |
| CH₃ | CH₃ | 2-CH₃O-phenyl | — |
| CH₃ | CH₃ | 2-CH₃S-phenyl | — |
| CH₃ | CH₃ | 2-benzyl-phenyl | — |
| CH₃ | CH₃ | 2,6-Cl₂-phenyl | — |
| CH₃ | CH₃ | 2,6-(CH₃)₂-phenyl | — |
| CH₃ | CH₃ | 3-Cl-phenyl | — |
| CH₃ | CH₃ | 3-CH₃-phenyl | — |
| CH₃ | CH₃ | 3-NO₂-phenyl | — |
| CH₃ | CH₃ | 4-F-phenyl | — |
| CH₃ | CH₃ | 4-CH₃O-phenyl | — |
| CH₃ | CH₃ | 4-(n-Bu)-phenyl | — |
| | —(CH₂)₄— | phenyl | — |
| | —(CH₂)₄— | 2-CH₃-phenyl | — |
| | —(CH₂)₅— | 2-CH₃-phenyl | — |
| | —(CH₂)₂O(CH₂)₂— | phenyl | — |
| | —(CH₂)₂O(CH₂)₂— | 2-F-phenyl | — |
| | —(CH₂)₂O(CH₂)₂— | 2-CH₃-phenyl | — |
| | —(CH₂)₂O(CH₂)₂— | 2-CF₃-phenyl | — |
| | —(CH₂)₂O(CH₂)₂— | 2-CH₃CH₂-phenyl | — |
| | —(CH₂)₂O(CH₂)₂— | 2-CH₃O-phenyl | — |

-continued

| R1 | R2 | R3 | R4 |
|---|---|---|---|
| | —(CH$_2$)$_2$O(CH$_2$)$_2$— | 2-CH$_3$S-phenyl | — |
| | —(CH$_2$)$_2$O(CH$_2$)$_2$— | 3-CH$_3$-phenyl | — |
| | —(CH$_2$)$_2$O(CH$_2$)$_2$— | 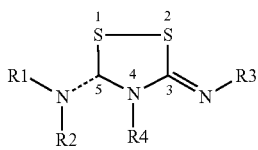 | — |
| —CH$_2$—CH(CH$_3$)OCH(CH$_3$)—CH$_2$— | | 2-F-phenyl | — |
| —CH$_2$—CH(CH$_3$)OCH(CH$_3$)—CH$_2$— | | 2-CH$_3$O-phenyl | — |
| —CH$_2$—CH(CH$_3$)OCH(CH$_3$)—CH$_2$— | | 2-CH$_3$CH$_2$-phenyl | — |
| | —(CH$_2$)$_2$S(CH$_2$)$_2$— | 2-F-phenyl | — |
| | —(CH$_2$)$_2$S(CH$_2$)$_2$— | 2-CH$_3$CH$_2$-phenyl | — |
| | —(CH$_2$)$_2$N(CH$_3$)(CH$_2$)$_2$— | 2-CH$_3$-phenyl | — |
| CH$_3$ | — | Cl | CH$_3$ |
| CH$_3$ | — | CH$_3$ | CH$_3$ |
| CH$_3$ | — | 2-(i-Pr)-phenyl | CH$_3$ |
| CH$_3$ | — | 2-CH$_3$O-phenyl | CH$_3$ |
| CH$_3$ | — | 2,6-Cl$_2$-phenyl | CH$_3$ |
| CH$_3$ | — | 3-F-phenyl | CH$_3$ |
| CH$_3$ | — | 4-F-phenyl | CH$_3$ |

4. A method for preparing a pharmaceutical composition comprising
   (i) combining a pharmacologically active amount of a compound of formula (I):

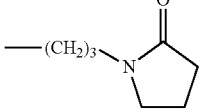

or a tautomer, stereoisomer, or N-oxide thereof, or a pharmacologically acceptable salt of any of the foregoing,
wherein the compound of formula (I) has anti-apoptotic activity, and
wherein the dotted lines represent single or double bonds, and wherein the compound of formula (I) is chosen from the compounds listed below:

| R1 | R2 | R3 | R4 |
|---|---|---|---|
| CH$_3$ | CH$_3$ | 2-pyridyl | — |
| CH$_3$ | CH$_3$ | 3-pyridyl | — |
| CH$_3$ | CH$_3$ | 2-F-phenyl | — |
| CH$_3$ | CH$_3$ | 2-CH$_3$-phenyl | — |
| CH$_3$ | CH$_3$ | 2-CF$_3$-phenyl | — |
| CH$_3$ | CH$_3$ | 2-CH$_3$CH$_2$-phenyl | — |
| CH$_3$ | CH$_3$ | 2-(i-Pr)-phenyl | — |
| CH$_3$ | CH$_3$ | 2-CH$_3$O-phenyl | — |
| CH$_3$ | CH$_3$ | 2-CH$_3$S-phenyl | — |
| CH$_3$ | CH$_3$ | 2-benzyl-phenyl | — |
| CH$_3$ | CH$_3$ | 2,6-Cl$_2$-phenyl | — |
| CH$_3$ | CH$_3$ | 2,6-(CH$_3$)$_2$-phenyl | — |
| CH$_3$ | CH$_3$ | 3-Cl-phenyl | — |
| CH$_3$ | CH$_3$ | 3-CH$_3$-phenyl | — |
| CH$_3$ | CH$_3$ | 3-NO$_2$-phenyl | — |
| CH$_3$ | CH$_3$ | 4-F-phenyl | — |
| CH$_3$ | CH$_3$ | 4-CH$_3$O-phenyl | — |
| CH$_3$ | CH$_3$ | 4-(n-Bu)-phenyl | — |
| | —(CH$_2$)$_4$— | 2-CH$_3$-phenyl | — |
| | —(CH$_2$)$_4$— | 2-C H$_3$-phenyl | — |
| | —(CH$_2$)$_5$— | 2-CH$_3$-phenyl | — |
| | —(CH$_2$)$_2$O(CH$_2$)$_2$— | phenyl | — |
| | —(CH$_2$)$_2$O(CH$_2$)$_2$— | 2-F-phenyl | — |
| | —(CH$_2$)$_2$O(CH$_2$)$_2$— | 2-CH$_3$-phenyl | — |
| | —(CH$_2$)$_2$O(CH$_2$)$_2$— | 2-CF$_3$-phenyl | — |
| | —(CH$_2$)$_2$O(CH$_2$)$_2$— | 2-CH$_3$CH$_2$-phenyl | — |
| | —(CH$_2$)$_2$O(CH$_2$)$_2$— | 2-CH$_3$O-phenyl | — |
| | —(CH$_2$)$_2$O(CH$_2$)$_2$— | 2-CH$_3$S-phenyl | — |
| | —(CH$_2$)$_2$O(CH$_2$)$_2$— | 3-CH$_3$-phenyl | — |
| | —(CH$_2$)$_2$O(CH$_2$)$_2$— | 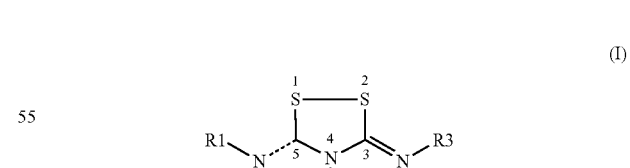 | — |
| —CH$_2$—CH(CH$_3$)OCH(CH$_3$)—CH$_2$— | | 2-F-phenyl | — |
| —CH$_2$—CH(CH$_3$)OCH(CH$_3$)—CH$_2$— | | 2-CH$_3$O-phenyl | — |
| —CH$_2$—CH(CH$_3$)OCH(CH$_3$)—CH$_2$— | | 2-CH$_3$CH$_2$-phenyl | — |
| | —(CH$_2$)$_2$S(CH$_2$)$_2$— | 2-F-phenyl | — |
| | —(CH$_2$)$_2$S(CH$_2$)$_2$— | 2-CH$_3$CH$_2$-phenyl | — |
| | —(CH$_2$)$_2$N(CH$_3$)(CH$_2$)$_2$— | 2-CH$_3$-phenyl | — |
| CH$_3$ | — | Cl | CH$_3$ |
| CH$_3$ | — | CH$_3$ | CH$_3$ |
| CH$_3$ | — | 2-(i-Pr)-phenyl | CH$_3$ |
| CH$_3$ | — | 2-CH$_3$O-phenyl | CH$_3$ |
| CH$_3$ | — | 2,6-Cl$_2$-phenyl | CH$_3$ |
| CH$_3$ | — | 3-F-phenyl | CH$_3$ |
| CH$_3$ | — | 4-F-phenyl | CH$_3$ | with at least one pharmaceutically acceptable carrier and/or at least one pharmaceutically acceptable auxiliary substance; and
   (ii) formulating the combination formed in (i) into a suitable form for administration.

5. A method of treating neurodegenerative diseases and other diseases characterized by free radical mediated cell degeneration and/or cell death (apoptosis) chosen from ischemic stroke, traumatic brain injury, amyotrophic lateral sclerosis (ALS), Alzheimer's disease, senile dementia, spinal cord injury, restless legs syndrome, Huntington's disease, Parkinson's disease, irritable bowel disease and inflammatory bowel diseases, Crohn's disease, ulcerative colitis, alcoholic hepatitis, liver cirrhosis, rheumatoid arthritis, multiple sclerosis, type 1 diabetes, acute and chronic rejection of heart-, lung-, kidney-, skin-, corneal-, bone marrow- or liver-transplants and tissue rejection, the method comprising administering a pharmaceutical composition comprising a pharmacologically active amount of a compound of formula (I)

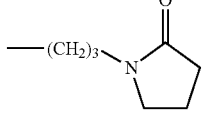

or a tautomer, stereoisomer, or N-oxide thereof, or a pharmacologically acceptable salt of any of the foregoing,
wherein the compound of formula (I) has anti-apoptotic activity, and
wherein the dotted lines represent single or double bonds, and wherein the compound of formula (I) is chosen from the compounds listed below:

| R1 | R2 | R3 | R4 |
|---|---|---|---|
| CH₃ | CH₃ | 2-pyridyl | — |
| CH₃ | CH₃ | 3-pyridyl | — |
| CH₃ | CH₃ | 2-F-phenyl | — |
| CH₃ | CH₃ | 2-CH₃-phenyl | — |
| CH₃ | CH₃ | 2-CF₃-phenyl | — |
| CH₃ | CH₃ | 2-CH₃CH₂-phenyl | — |
| CH₃ | CH₃ | 2-(i-Pr)-phenyl | — |
| CH₃ | CH₃ | 2-CH₃O-phenyl | — |
| CH₃ | CH₃ | 2-CH₃S-phenyl | — |
| CH₃ | CH₃ | 2-benzyl-phenyl | — |
| CH₃ | CH₃ | 2,6-Cl₂-phenyl | — |
| CH₃ | CH₃ | 2,6-(CH₃)₂-phenyl | — |
| CH₃ | CH₃ | 3-Cl-phenyl | — |
| CH₃ | CH₃ | 3-CH₃-phenyl | — |
| CH₃ | CH₃ | 3-NO₂-phenyl | — |
| CH₃ | CH₃ | 4-F-phenyl | — |
| CH₃ | CH₃ | 4-CH₃O-phenyl | — |
| CH₃ | CH₃ | 4-(n-Bu)-phenyl | — |
| —(CH₂)₄— | | 2-CH₃-phenyl | — |
| —(CH₂)₄— | | 2-CH₃-phenyl | — |
| —(CH₂)₅— | | 2-CH₃-phenyl | — |
| —(CH₂)₂O(CH₂)₂— | | phenyl | — |
| —(CH₂)₂O(CH₂)₂— | | 2-F-phenyl | — |
| —(CH₂)₂O(CH₂)₂— | | 2-CH₃-phenyl | — |
| —(CH₂)₂O(CH₂)₂— | | 2-CF₃-phenyl | — |
| —(CH₂)₂O(CH₂)₂— | | 2-CH₃CH₂-phenyl | — |
| —(CH₂)₂O(CH₂)₂— | | 2-CH₃O-phenyl | — |
| —(CH₂)₂O(CH₂)₂— | | 2-CH₃S-phenyl | — |
| —(CH₂)₂O(CH₂)₂— | | 3-CH₃-phenyl | — |
| —(CH₂)₂O(CH₂)₂— | | —(CH₂)₃–N-pyrrolidinone | — |
| —CH₂—CH(CH₃)OCH(CH₃)—CH₂— | | 2-F-phenyl | — |
| —CH₂—CH(CH₃)OCH(CH₃)—CH₂— | | 2-CH₃O-phenyl | — |
| —CH₂—CH(CH₃)OCH(CH₃)—CH₂— | | 2-CH₃CH₂-phenyl | — |
| —(CH₂)₂S(CH₂)₂— | | 2-F-phenyl | — |
| —(CH₂)₂S(CH₂)₂— | | 2-CH₃CH₂-phenyl | — |
| —(CH₂)₂N(CH₃)(CH₂)₂— | | 2-CH₃-phenyl | — |
| CH₃ | — | Cl | CH₃ |
| CH₃ | — | CH₃ | CH₃ |
| CH₃ | — | 2-(i-Pr)-phenyl | CH₃ |
| CH₃ | — | 2-CH₃O-phenyl | CH₃ |
| CH₃ | — | 2,6-Cl₂-phenyl | CH₃ |
| CH₃ | — | 3-F-phenyl | CH₃ |
| CH₃ | — | 4-F-phenyl | CH₃ | to a patient in need of such treatment.

6. A method of treating neurodegenerative diseases and other diseases characterized by free radical mediated cell degeneration and/or cell death (apoptosis) chosen from ischemic stroke, traumatic brain injury, amyotrophic lateral sclerosis (ALS), Alzheimer's disease, senile dementia, spinal cord injury, restless legs syndrome, Huntington's disease, Parkinson's disease, irritable bowel disease and inflammatory bowel diseases, Crohn's disease, ulcerative colitis, alcoholic hepatitis, liver cirrhosis, rheumatoid arthritis, multiple sclerosis, type 1 diabetes, acute and chronic rejection of heart-, lung-, kidney-, skin-, corneal-, bone marrow- or liver-transplants and tissue rejection, the method comprising administering to a patient in need of such treatment a pharmaceutical composition comprising a pharmacologically active amount of a compound of formula (I):

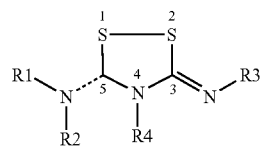

(I)

or a tautomer, stereoisomer, or N-oxide thereof, or a pharmacologically acceptable salt of any of the foregoing, wherein the compound of formula (I) has anti-apoptotic activity, and wherein the dotted lines between carbon atom number 5 and its neighboring nitrogen atoms represent single or double bonds, with the proviso that one of the two bonds is a single bond and one is a double bond, and with the proviso that when the double bond is between carbon atom number 5 and nitrogen atom number 4, R4 does not exist and when the double bond is between carbon atom number 5 and the exo-nitrogen atom, R2 does not exist, R1, R2, R3 and R4 independently are chosen from a branched or unbranched alkyl($C_{1-4}$ group, optionally containing sulphur atoms or sulphoxide, amide, ketone, thioketone or sulfone groups, and optionally substituted with halogen, cyano, mono- or dialkyl($C_{1-4}$)amino, trifluoromethyl, ($C_{1-4}$-alkoxy or hydroxyl groups; or R1 and R2 together with the nitrogen atom to which they are attached, form a 4 to 8 membered ring system wherein the ring system optionally comprises other (substituted) hetero atoms chosen from N, O and S, and which ring system may be optionally substituted with branched or unbranched alkyl($C_{1-4}$, halogen, cyano, mono- or dialkyl($C_{1-4}$)amino, trifluoromethyl, ($C_{1-4}$-alkoxy or hydroxyl or which ring system contains amide, ketone, thioketone, sulfone or sulfoxide functions;

R3 is chosen from a hydrogen atom, and a branched or unbranched alkyl($C_{1-4}$ group, optionally containing sulphur atoms or sulphoxide, amide, ketone, thioketone or sulfone groups, and optionally substituted with halogen, cyano, mono- or dialkyl($C_{1-4}$-amino, trifluoromethyl, ($C_{1-4}$alkoxy, S-alkyl($C_{1-4}$, SH or hydroxyl groups; or R3 is an aryl group, optionally substituted with branched or unbranched alkyl($C_{1-4}$), aryl, alkyl($C_{1-4}$aryl, SH, S-alkyl($C_{1-4}$, halogen, cyano, mono- or dialkyl($C_{1-4}$) amino, $CF_3$, $OCF_3$, $SCF_3$, nitro, hydroxy or ($C_{1-4}$alkoxy groups.

* * * * *

UNITED STATES PATENT AND TRADEMARK OFFICE
CERTIFICATE OF CORRECTION

PATENT NO. : 7,678,789 B2
APPLICATION NO. : 11/349910
DATED : March 16, 2010
INVENTOR(S) : Feenstra et al.

Page 1 of 2

It is certified that error appears in the above-identified patent and that said Letters Patent is hereby corrected as shown below:

Claim 2, col. 15, line 57, delete
"-(CH$_2$)$_4$-          2-CH$_3$-phenyl"
and insert therefor
-- -(CH$_2$)$_4$-          phenyl--.

Claim 4, col. 17, line 65, delete
"-(CH$_2$)$_4$-          2-CH$_3$-phenyl"
and insert therefor
-- -(CH$_2$)$_4$-          phenyl--.

Claim 5, col. 19, line 20, delete
"-(CH$_2$)$_4$-          2-CH$_3$-phenyl"
and insert therefor
-- -(CH$_2$)$_4$-          phenyl--.

Claim 6, col. 20, line 29, "alkyl(C$_{1-4}$ group" should read --alkyl(C$_{1-4}$) group--.

Claim 6, col. 20, line 33, "(C$_{1-4}$-alkoxy" should read --(C$_{1-4}$)-alkoxy--.

Claim 6, col. 20, line 39, "alkyl(C$_{1-4}$" should read --alkyl(C$_{1-4}$)--.

Claim 6, col. 20, lines 40-41, "(C$_{1-4}$-alkoxy" should read --(C$_{1-4}$)-alkoxy--.

Claim 6, col. 20, line 48, "(C$_{1-4}$-amino" should read --(C$_{1-4}$)-amino--.

Claim 6, col. 20, line 49, "(C$_{1-4}$-alkoxy" should read --(C$_{1-4}$)-alkoxy--.

Claim 6, col. 20, line 51, "(C$_{1-4}$-aryl" should read --(C$_{1-4}$)-aryl--.

Claim 6, col. 20, line 52, "S-alkyl(C$_{1-4}$," should read --S-alkyl(C$_{1-4}$),--.

Signed and Sealed this

Twenty-seventh Day of July, 2010

David J. Kappos
*Director of the United States Patent and Trademark Office*

Claim 6, col. 20, line 53, "($C_{1-4}$-alkoxy" should read --($C_{1-4}$)-alkoxy--.